United States Patent
Bowman

(10) Patent No.: US 6,689,081 B2
(45) Date of Patent: Feb. 10, 2004

(54) RIGID ANKLE AND FOOT ORTHOSIS

(76) Inventor: Gerald D. Bowman, 19820 Ingomar St., Winnetka, CA (US) 91306

( * ) Notice: Subject to any disclaimer, the term of this patent is extended or adjusted under 35 U.S.C. 154(b) by 0 days.

(21) Appl. No.: 09/947,493

(22) Filed: Sep. 5, 2001

(65) Prior Publication Data

US 2002/0029009 A1 Mar. 7, 2002

Related U.S. Application Data

(60) Provisional application No. 60/230,624, filed on Sep. 5, 2000.

(51) Int. Cl.⁷ ............................... A61F 5/00; A61F 5/37
(52) U.S. Cl. ............................ 602/27; 602/16; 128/882
(58) Field of Search ..................... 602/16, 27, 28–29; 128/882

(56) References Cited

U.S. PATENT DOCUMENTS

| | | | | |
|---|---|---|---|---|
| 4,934,355 A | * | 6/1990 | Porcelli | 602/16 |
| 5,031,607 A | * | 7/1991 | Peters | 2/22 |
| 5,209,722 A | * | 5/1993 | Miklaus et al. | 602/27 |
| 5,242,379 A | * | 9/1993 | Harris et al. | 602/16 |
| 5,445,603 A | * | 8/1995 | Wilkerson | 602/27 |
| 5,542,774 A | * | 8/1996 | Hoy | 403/113 |
| 5,571,078 A | * | 11/1996 | Malewicz | 128/882 |
| 5,676,642 A | * | 10/1997 | Peters | 602/23 |
| 5,759,168 A | * | 6/1998 | Bussell et al. | 602/27 |
| 5,797,865 A | * | 8/1998 | McDavid, III | 602/16 |
| 5,902,259 A | * | 5/1999 | Wilkerson | 602/16 |
| 5,944,678 A | * | 8/1999 | Hubbard | 602/27 |
| 5,944,679 A | * | 8/1999 | DeToro | 602/16 |
| 5,971,946 A | * | 10/1999 | Quinn et al. | 602/27 |
| 6,053,884 A | * | 4/2000 | Peters | 602/16 |
| 6,146,350 A | * | 11/2000 | Morton | 602/16 |
| 6,485,447 B1 | * | 11/2002 | Lavery et al. | 602/23 |

* cited by examiner

Primary Examiner—Nicholas D. Lucchesi
Assistant Examiner—Fenn C Mathew
(74) Attorney, Agent, or Firm—Robert Louis Finkel

(57) ABSTRACT

A therapeutic ankle and foot orthosis or brace includes a lower shell and an upper lateral shell which are movably coupled together by a pivot so that the shells accommodate the contour, size and shape of the user's foot and ankle. Cushions are included on the shells to provide comfort and straps with hook and pile fasteners are employed to detachably retain the combined shells on the ankle and foot of the user.

4 Claims, 2 Drawing Sheets

RIGID ANKLE AND FOOT ORTHOSIS

This application claims benefit of Provisional application Serial No. 60/230,624 filed Sep. 5, 2000.

BACKGROUND OF THE INVENTION

1. Field of the Invention

The present invention relates to the field of ankle and foot orthosis and more particularly to rigid ankle and foot orthosis used in athletic and medical applications for individuals who have injured their ankle or have an unstable ankle joint.

2. Brief Description of the Prior Art

Ankle orthoses and ankle and foot orthoses have become a popular form of treatment for controlling lateral ankle motion in the injured or unstable ankle. Lateral ankle injuries account for the majority of ankle injuries. These injured ankles have a high probability of suffering recurring sprains and increased joint laxity. The ankle joint is an articulation involving the tibia and fibular with the talus. The talus also forms a major articulation with the calcaneus (sub-talor joint). As the ankle joint is very intimately connected to the sub-talor joint in the foot, an ankle and foot orthosis must ideally control lateral ankle motion (inversion) and sub-talor joint motion (supination). In addition, for an orthoses to be considered functional, it must minimally restrict all other motions including plantarflexion/dorsiflexion at the ankle (up/down motion of the foot) and natural pronation of the foot (inward rotation with flattening of the arch). An orthosis that can achieve all these criteria can represent a significant improvement in function.

Rigid ankle bracing was popularized by the "aircast" stirrup ankle brace described by Johnson, Jr., U.S. Pat. No. 4,280,489. This discloses an orthosis consisting of two outer injection molded plastic shells (commonly referred to as "stirrups") with two inner inflatable air bags/bladders. The shells lie against the medial side and lateral side of the heel, ankle and lower leg and are connected above the ankle by two Velcro® straps and are connected distally by a strap under the heel.

Prior Patents to Grim, (U.S. Pat. Nos. 4,844,094; 5,092,319; 5,348,530; 5,445,602); Brewer, U.S. Pat. No. 4,966,134; Hess, U.S. Pat. No. 5,038,762; Johnson, Jr., (U.S. Pat. Nos. 5,125,400; 5,389,065); Makinen, U.S. Pat. No. 5,199,941; Montag, U.S. Pat. No. 5,472,411; Morris, U.S. Pat. No. 5,501,659; Iglasias, (U.S. Pat. Nos. 5,716,335; 5,951,504) all disclose similar stirrup arrangements with differing padding and/or strapping mechanisms and/or adjustments to the shapes of the shells.

Alternatively, Peters, U.S. Pat. No. 4,510,927 disclosed a variation to the traditional stirrup design by utilizing the addition of a medial and a lateral hinge placed at the level of the anatomical ankle joint axis. Peters, (U.S. Pat. Nos. 5,031,607; 5,366,439; 5,836,903; 6,053,884); Swearington, U.S. Pat. No. 5,056,509, Prock, U.S. Pat. No. 5,069,202; Miklaus, U.S. Pat. No. 5,209,072; Harris, U.S. Pat. No. 5,242,379; Wehr, U.S. Pat. No. 5,503,622; McDavid, U.S. Pat. No. 5,797,865; Quinn, U.S. Pat. No. 5,971,946 all disclose variations to the hinged stirrup design, varying essentially by any combination of changes to the shape/position of the shells, strapping mechanism and/or padding mechanism.

Others have disclosed single hinged devices. Nelson, U.S. Pat. No. 4,719,926 and Wilkerson, U.S. Pat. No. 5,445,603 disclose lateral hinged stirrup orthoses. Wilkerson, U.S. Pat. No. 5,902,259 also discloses a medial hinged stirrup device. This device has a medial hinge and a lateral supporting structure with a lateral malleolar aperture. However, this device fails to extend over the latero-superior aspect of the talar head and therefore lacks supination control. Also, the device extends much higher on the lateral aspect of the leg applying pressure to the fibular shaft and neck and does not rigidly connect the footplate to the lateral support structure.

All of the prior art orthoses are flawed by any combination of the following defects: loss of intimate contact on the medial calcaneus; loss of intimate contact on/around the fibular malleolus; no force application over the latero-superior aspect of the talar head; loss of rigidity in the medial lever; lack of a distal counteractive force on the forefoot needed to control rotation of the talus; restriction of dorsiflexion and/or plantarflexion; restriction of functional pronation.

SUMMARY OF THE INVENTION

Accordingly, the above problems and difficulties are avoided by the rigid ankle and foot orthosis presented herein as the inventive device or brace applies forces to specific areas of the ankle and foot to effectively limit lateral motion of the fibular malleolus (inversion) and lateral/superior rotation of the talus (supination) while avoiding any unnecessary additional contact and allowing all other motions of the foot and ankle to be unrestricted.

In one form of the invention, the orthosis or brace includes two contoured semi-rigid plastic shells. A medial/plantar/lateral shell extends from the medial malleolus down under the foot and then up over the fibular malleolus and the latero-superior aspect of the talus. An aperture in the shell lies in the area of the fibular malleolus. The lateral section and aperture are covered interiorly by a cushioning pad of a non-elastic nature to cushion the malleolus and prevent lateral displacement. Superiorly, the lateral section forms a bridge between the posterior and anterior margins to avoid pressure on the fibular shaft and neck. A stirrup shaped medial shell lies against the medial aspect of the cibia and connects to the medial portion of the medial/plantar/lateral shell. Interiorly disposed of this shell lies a cushioning pad. A screw or pin connects the two plastic shells forming a pivot hinge and is placed at the position of the anatomical ankle axis. An additional pivot or screw connects the two shells and slides through an arcuate slot in the medial shell. Three straps connectably fasten the orthosis to the ankle and foot.

Therefore, a primary object of the present invention is to provide an ankle and foot orthosis that effectively limits lateral fibular malleolar displacement, i.e. inversion. Another object of the present invention is to provide an ankle and foot orthosis that effectively limits latero-superior rotation of the talus, i.e. supination. A still further object of the present invention is to provide an ankle or foot orthosis that has minimal resistance to all other motions, namely plantarflexion, dorsiflexion and pronation.

An even further object of the present invention is to provide an ankle and foot brace that has minimal contact on the leg, ankle and foot by avoiding unnecessary contact thereby keeping the bulk of the orthosis to a minimum and allowing easy fitting into a users shoe.

A further object of the present invention is to provide a comfortable, inexpensive ankle orthosis that can be economically manufactured.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 4 is a front elevational view of the ankle and foot orthosis or brace.

DESCRIPTION OF PREFERRED EMBODIMENT

Figure 1:
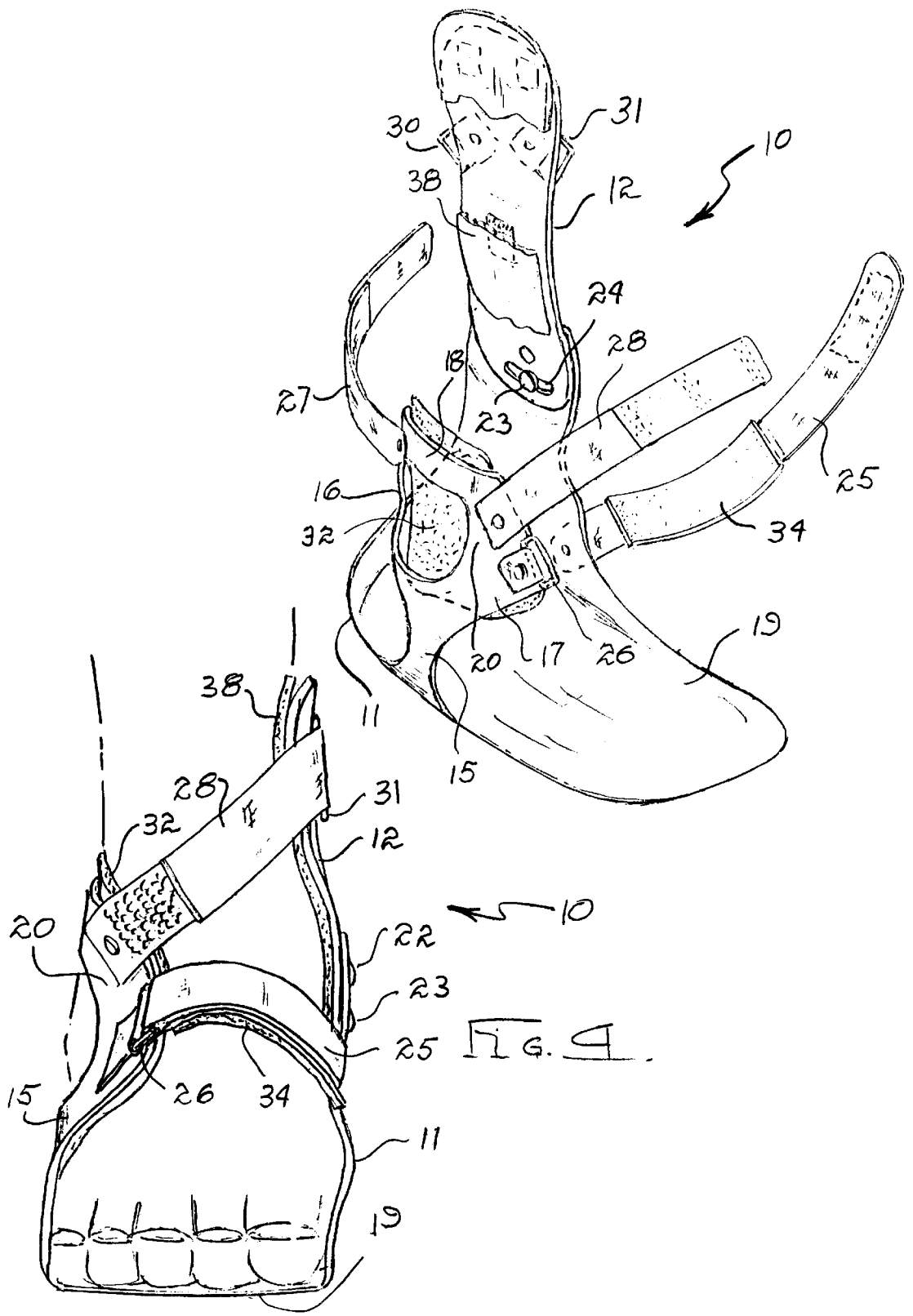
FIG. 1 is a front perspective view of the ankle and foot orthosis or brace incorporating the present invention.
Figure 2:
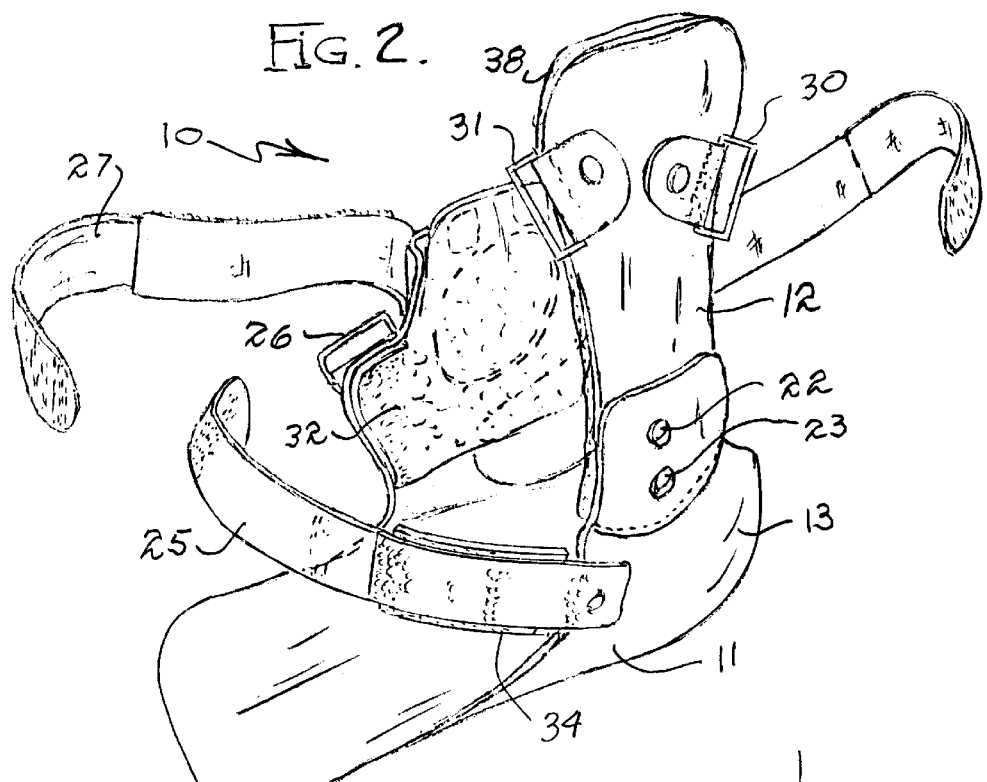
FIG. 2 is a perspective view similar to the view shown in FIG. 1, as taken from the opposite side thereof.
Figure 3:
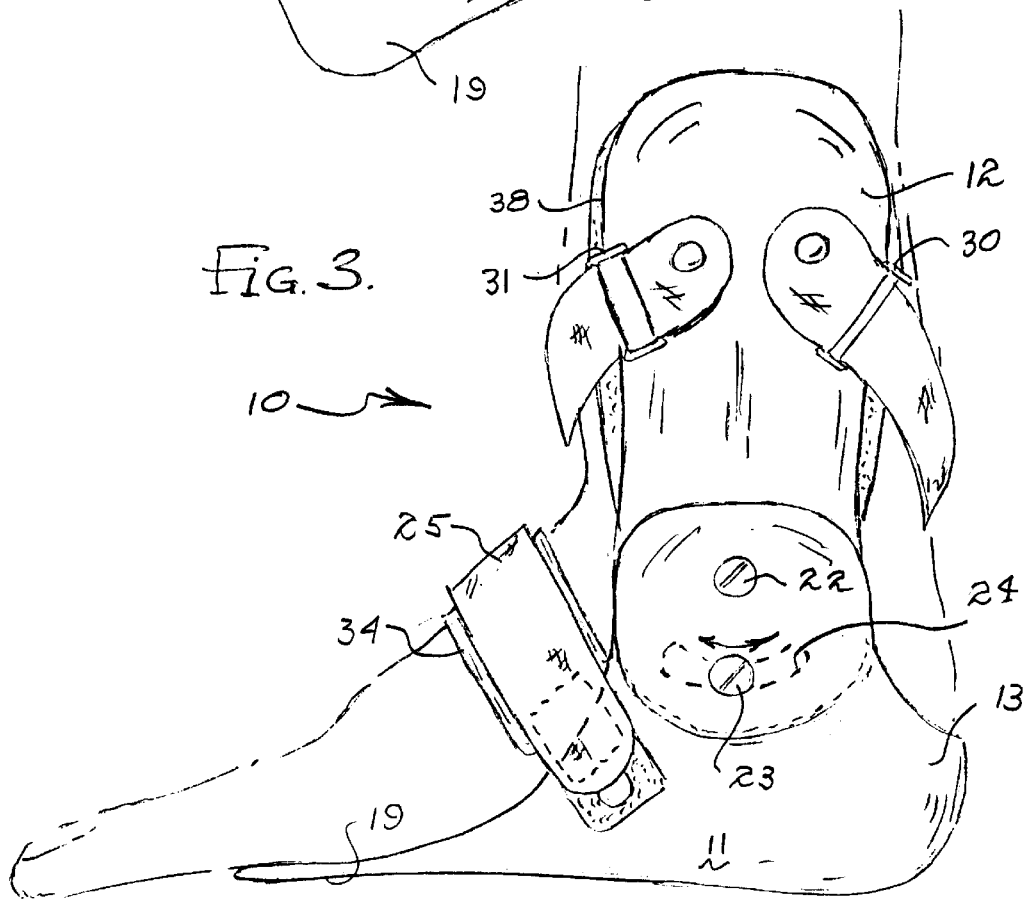
FIG. 3 is a side elevational or medial view of the ankle and foot orthosis or brace as worn on a right foot and ankle.

Referring in detail to FIGS. 1 and 2, the ankle and foot orthosis or brace of the present invention is illustrated in the direction of arrow 10 which includes a medial/plantar/lateral plastic shell 11 and a contoured medial plastic shell 12.

FIG. 2 illustrates the medial section 13 of the medial/plantar/lateral shell which encompasses the medial calcaneus and extends upwards to encompass the medial malleolus. Its anterior margin lies at the level of the anterior margin of the medial malleolus. Posteriorly it extends upwards at an angle. Just below the medial malleolus it forms a raised area to accommodate the interconnecting medial shell 12. In its raised area it has two small apertures for receiving a pivot screw 22 and a screw 23 to provide stability to the medial aspect of the structure.

FIG. 2 shows a lateral section of the medial/plantar/lateral shell as it forms a strut 15 extending up out of the footplate 19 in an area approximating the front of the calcaneus to the base of the 5th metatarsal. Just below the fibular malleolus the device forms a "Y" shape whereby it extends posteriorly to beyond the posterior margin of the fibular malleolus section 16 and extends anteriorly beyond the anterior margin of the fibular malleolus and past the latero-superior aspect of a talar head section 17. Superior margin section 18 forms a bridged/raised area connecting an anterior section 20 and a posterior section 16. The lateral section has an aperture 21 in the middle corresponding to the position of the fibular malleolus.

Viewed posteriorly, the medial/plantar/lateral shell 11 forms an approximate "U" shape that has a medial extension 13, a plantar footplate section 19, and lateral sections 15, 16 and 18.

The medial shell 12 forms a stirrup shape and extends from the inferior margin of the medial malleolus to the lower calf region. Towards its inferior margin lies the small aperture and arcuate slot 24 for receiving the pivot screw 22 and screw 23 that connect it to the medial section 13 of the medial/plantar/lateral shell 11.

The latero-superior talar support area 17 shown in FIG. 1 is secured to the foot by a Velcro® fastening strap 25 that originates from the anterior margin of the medial section 13 of the medial/plantar/lateral shell 11 and reverses through a "D" ring 26 attached to the talar support area 17.

The posterior fibular malleolar support area 20 and anterior fibular malleolar support area 16 are secured to the ankle by two hook and pile fastening straps 27 and 28 that originate at the posterior fibular malleolar support area 20 and anterior fibular malleolar support area 16 respectively and reverse through two "D" rings 30 and 31 on the medial shell 12.

Interiorly disposed of the lateral sections 20, 16, 18, 21 and 17 of the medial/plantar/lateral shell 11 lies a cushioning pad 32 sized to follow the outline of the shell and extend marginally beyond and across the aperture 21. Interiorly disposed of the medial shell 12 lies a cushioning pad 33 sized to follow the outline of the shell and extend marginally beyond. Another cushion pad 34 lies on the backside of strap 25.

In view of the foregoing, it can be seen that the novel ankle and foot orthosis or brace includes a two-piece construction, a lower shell 11 and an upper medial shell 12. The shells are joined together by pivot fastener 22 and screw 23. The lower shell includes a forward extending portion that projects substantially under the forward sole of the user's foot. Strap 28 is angularly disposed across the front of the ankle adjustably joining the two shells together. Additionally, foot strap 25 detachably connects the shells together to further stabilize the shells on the user's foot. The cushions, which may be air pads or gel, provide comfort and the hook and pile fasteners provide ready adjustment to accommodate contour, shape and size of the user's foot. Since the shell 11 includes medial and lateral sections 15, 20 and 13 separated by the user's foot, a unitary construction is produced to provide stability and improved support. The elongated upper shell 12 extends quite high on the outside of the leg which places desirable pressure on the leg.

Therefore, the present invention provides an ankle and foot orthosis for the stabilization of inversion and supination and includes a molded plastic foot and ankle shell shaped to extend along the plantar aspect of the foot disposed around the medial aspect of the calcaneus and over the medial malleolus. The shell further extends laterally around the fibular head with a fibular neck bridge and up over the latero-superior aspect of the talar head (medial/plantar/lateral shell). The leg shell is molded and is shaped to extend from the medial malleoli area to the lower calf region. The medial pivot hinge or screws connect the two shells while fastening straps hold the shells in place of the user's foot and leg while maintaining application of forces. The screws and arcuate slot provide stability to the medial aspect of the structure. The brace has free dorsiflexion/plantarflexion, motion at the ankle (up/down motion of the foot).

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. An orthotic device to be worn for limiting inversion and supination of the wearer's ankle joint and foot comprising:

a unitary, generally "U" shape ankle and foot shell embracing the wearer's heel and extending under and embracing the wearer's foot, said shell having an upstanding medial portion embracing the inside of the wearer's ankle and an upstanding lateral portion embracing, and having an aperture therein retaining, the outside of the wearer's ankle, a portion of the lateral portion extending anteriorly of the wearer's ankle and supportingly embracing the laterally facing portion of the wearer's instep;

an elongated leg shell pivotably mounted to the upstanding medial portion of said ankle and foot shell and supportingly embracing the inside of the wearer's leg;

selectively adjustable first coupling means extending anteriorly of the wearer's ankle and connecting the upstanding lateral portion of said ankle and foot shell with said leg shell;

selectively adjustable second coupling means extending posteriorly of the wearer's ankle and connecting the upstanding lateral portion of said ankle and foot shell with said leg shell; and selectively adjustable third coupling means extending across the medially facing portion of the wearer's instep and connecting the anteriorly extending portion of the lateral portion of said ankle and foot shell with the medial portion of said ankle and foot shell.

2. An orthotic device according to claim 1, wherein said elongated leg shell is mounted for limited rotation to the upstanding medial portion of said ankle and foot shell.

3. An orthotic device according to claim 1, wherein said first, second and third coupling means are hook and pile fastening straps individually selectively adjustable for limiting inversion of the wearer's ankle joint and supination of the wearer's foot.

4. An orthotic device to be worn for limiting inversion and supination of the wearer's ankle joint and foot comprising:

a unitary, resilient, generally "U" shape ankle and foot shell embracing the wearer's heel and extending under and embracing the wearer's foot, said shell having an upstanding medial portion supportingly embracing the inside of the wearer's ankle and an upstanding lateral portion supportingly embracing, and having an aperture therein retaining, the outside of the wearer's ankle, a portion of the lateral portion extending anteriorly of the wearer's ankle and supportingly embracing the laterally facing portion of the wearer's instep;

an elongated, unitary, resilient leg shell mounted for limited pivoting motion to the upstanding medial portion of said ankle and foot shell and supportingly embracing the inside of the wearer's leg, said upstanding lateral portion and said leg shell comprising inner surfaces the surfaces having cushions affixed thereto;

a selectively adjustable first fastening strap extending anteriorly of the wearer's ankle and connecting the upstanding lateral portion of said ankle and foot shell with said leg shell;

a selectively adjustable second fastening strap extending posteriorly of the wearer's ankle and connecting the upstanding lateral portion of said ankle and foot shell with said leg shell; and a selectively adjustable third fastening strap extending across the wearer's instep and connecting the portion of said ankle and foot shell extending anteriorly of the wearer's ankle with the medial portion of said ankle and foot shell.

\* \* \* \* \*